United States Patent
Shin et al.

(10) Patent No.: US 7,041,126 B2
(45) Date of Patent: May 9, 2006

(54) FLEXIBLE SELF-EXPANDABLE STENT AND METHOD OF PRODUCING THE SAME

(75) Inventors: Kyong-Min Shin, 265-80, Hongeun-3-dong, Seodaemun-ku, Seoul, 157-765 (KR); Jeong-Hee Nam, Kwangmyung-si (KR); Jin-Hong Kim, Yongin-si (KR)

(73) Assignees: Taewoong Medical Co., Ltd., Koyang-si (KR); Kyong-Min Shin, Seoul (KR)

( * ) Notice: Subject to any disclaimer, the term of this patent is extended or adjusted under 35 U.S.C. 154(b) by 90 days.

(21) Appl. No.: 10/653,695

(22) Filed: Sep. 2, 2003

(65) Prior Publication Data

US 2004/0236401 A1 Nov. 25, 2004

(30) Foreign Application Priority Data

May 23, 2003 (KR) ...................... 10-2003-0032928

(51) Int. Cl.
*A61F 2/06* (2006.01)

(52) U.S. Cl. .................. 623/1.13; 623/1.44; 623/1.51; 623/1.53

(58) Field of Classification Search ............... 623/1.15, 623/1.18, 1.2, 1.32, 1.33, 1.44, 1.53, 1.13
See application file for complete search history.

(56) References Cited

U.S. PATENT DOCUMENTS

| | | | | |
|---|---|---|---|---|
| 5,522,881 | A | * | 6/1996 | Lentz .......................... 623/1.13 |
| 5,667,523 | A | * | 9/1997 | Bynon et al. ............... 623/1.13 |
| 5,718,159 | A | * | 2/1998 | Thompson ..................... 87/33 |
| 6,168,619 | B1 | * | 1/2001 | Dinh et al. ................. 623/1.13 |

\* cited by examiner

*Primary Examiner*—Alvin J. Stewart
*Assistant Examiner*—Christopher Prone
(74) *Attorney, Agent, or Firm*—Ladas & Parry LLP

(57) ABSTRACT

A flexible self-expandable stent has inside and outside stent bodies each fabricated by knitting first and second superelastic shape memory alloy wires into a net-like structure with the first wire zigzagged with a diagonal length P interlocked with the second wire zigzagged with a diagonal length 2P at a plurality of interlocked points with intersecting points therebetween to allow the stent bodies to apply force against longitudinal contraction of the stent bodies. The interlocked points and the intersecting points form a plurality of diamond-shaped meshes in the net-like structure of each stent body. A hollow rubber tube is closely fitted between the inside and outside stent bodies, with each of the overlapped ends of the rubber tube and the stent bodies being integrating into a single structure.

2 Claims, 6 Drawing Sheets

FLEXIBLE SELF-EXPANDABLE STENT AND METHOD OF PRODUCING THE SAME

BACKGROUND OF THE INVENTION

1. Field of the Invention

The present invention relates to flexible self-expandable stents made of super-elastic shape memory alloys and used for insertion in the desired parts of contracted muscular passages, contracted blood vessels, or arteries having an aneurysm so as to open the contracted parts or repair the arterial dilatation and, more particularly, to a flexible self-expandable stent, designed to maintain a shape thereof corresponding to the desired part of a contracted muscular passage, a contracted blood vessel, or an artery having an aneurysm, thus being effectively used for opening the contracted part or repairing the arterial dilatation, without deforming the shape of the contracted muscular passage, the contracted blood vessel, or the dilated artery, regardless of the shape of the contracted muscular passage, the contracted blood vessel, or the dilated artery. The present invention also relates to a method of producing such flexible self-expandable stents.

2. Description of the Related Art

Generally, blood vessels, in particular, arteries may be contracted at a part thereof due to thrombus, arteriosclerosis or the like to have angiostenosis, and may be dilated at a part thereof due to senility and/or some diseases with an aneurysm which is the arterial dilatation.

A surgical operation has been typically performed for treating the contracted artery or repairing the arterial dilatation through an artificial vessel replacement in which the contracted or dilated artery is replaced with an artificial blood vessel or through angioplasty. However, since the surgical operation for treating the contracted artery or repairing the arterial dilatation through the artificial vessel replacement or the angioplasty must be accompanied by making a large incision in the skin of a patient around the contracted or dilated artery, the operation undesirably leaves a large, ugly scar on the skin and mars the appearance of the patient. The surgical operation is also problematic in that it does not accomplish a desired operational effect.

The above-mentioned problems, experienced in the surgical operation for treating the contracted artery or repairing the arterial dilatation, are also caused in the artificial vessel replacement or the angioplasty to treat the stenosis of the gullet, the gall duct, the urethra, the formation of the artificial passage in the jugular vein, and the stenosis and blockade of the internal organs.

In an effort to overcome these problems, a variety of techniques to simply treat the contracted parts or repair the arterial dilatation, without surgery, have been proposed. One of the proposed techniques is the use of self-expandable stents made of a shape memory alloy.

The conventional self-expandable stent, used for insertion in a desired part of a contracted muscular passage, a contracted blood vessel, or an artery having an aneurysm to open the contracted part or repair the arterial dilatation, comprises a cylindrical stent body which is fabricated by knitting a plurality of shape memory alloy wires with each other to form a net-like hollow cylindrical body having a predetermined length and a plurality of diamond-shaped meshes.

To prevent an infiltration of tumor cells into the interior of the self-expandable stent and prevent undesired contact of a material, such as food, with the lesion, and allow the stent to reliably repair the arterial dilatation, the cylindrical stent body is provided with a coat layer on the external surface thereof to externally cover the sidewall of the stent body.

In such a case, the coat layer may be formed on the stent body by immersing the stent body in polytetrafluoroethylene (PTFE).

To place the self-expandable stent in a desired part of a contracted muscular passage or a dilated artery, the hollow cylindrical stent body is considerably reduced in volume by compressing the meshes of the stent body, and is inserted into the desired part of the contracted muscular passage or the dilated artery by using a stent inserting device, such as a catheter. When the compressed stent body is placed in the desired part, the stent body made of the shape memory alloy wires restores its original shape, thus opening the contracted part or repair the arterial dilatation.

However, the conventional self-expandable stents are problematic in that the stents are not preferably used in the bent parts of the contracted muscular passages or the dilated arteries, so that the usability of the stents is reduced.

That is, when the self-expandable stent is inserted into a bent part of a contracted muscular passage or a dilated artery, the stent does not maintain a desired bent shape corresponding to the bent part of the contracted muscular passage or the dilated artery, but restores its horizontal or vertical straight shape, thus lengthening the contracted or dilated part of the muscular passage or the artery and deforming the bent shape of the contracted or dilated part into a horizontal or vertical straight shape. The muscular passage or the dilated artery may be deformed to be narrower than its original size due to the stent, thereby hindering the circulation of a material, such as food or blood, and deteriorating the function of the stents.

In an effort to overcome the above-mentioned problems experienced in the conventional expandable stents, the inventor of the present invention proposed a flexible self-expandable stent which maintains a desired bent shape thereof corresponding to a desired part of a contracted muscular passage or a dilated artery, as disclosed in Korean Patent No. 2001-180245. As shown in FIGS. 1 to 3 of the accompanying drawings, the flexible self-expandable stent disclosed in Korean Patent No. 2001-180245 comprises a hollow cylindrical stent body which is fabricated by knitting first and second super-elastic shape memory alloy wires 10 and 11 to make a net-like structure 50 in that the first wire 10, which is zigzagged with a diagonal length P in a longitudinal direction of the stent body, is interlocked with the second wire 11, which is zigzagged with a diagonal length 2P in the longitudinal direction, at different positions to form a plurality of interlocked points 60 capable of allowing the stent body to contract and expand in the longitudinal direction. The net-like structure 50 also has a plurality of intersecting points 70 which are formed by a repeated intersection of the first and second wires 10 and 11 at a plurality of positions between the interlocked points 60. The intersecting points 70 allow the stent body to apply a force against the longitudinal contraction of the stent body. In the net-like structure 50, the interlocked points 60 and the intersecting points 70 define a plurality of diamond-shaped meshes 20.

The first and second wires 10 and 11 are thus interlocked with each other to be prevented from being separated from each other while allowing the stent body to somewhat freely contract and expand.

The wires 10 and 11 are produced by using a shape memory alloy through the steps of producing wires by shaping an alloy of harmless metals into a desired shape, and heat-treating the wires to allow the wires to restore the original shapes thereof at a predetermined temperature.

In such a case, the heat treatment for the shape memory alloy wires 10 and 11 is preferably performed at about 350° C.~600° C. for 8~30 min, as disclosed in Korean Patent No. 2001-180245.

The flexible self-expandable stent is preferably fabricated by using two shape memory alloy wires 10 and 11 each having a diameter ranging from 0.1 mm to 0.5 mm. When the diameter of the wires 10 and 11 is less than 0.1 mm, the wires 10 and 11 only have insufficient elasticity, so that the stent cannot effectively open a contracted or dilated part of the muscular passage or the artery. When the diameter of the wires 10 and 11 exceeds 0.5 mm, the meshes 20 of the stent body do not have sufficient space, so that it is almost impossible to reduce the volume of the stent to a desired level when the stent is inserted into a desired part of the contracted muscular passage or the dilated artery.

In the flexible self-expandable stent, it is necessary to set the number of bent parts 30, provided at each end of the stent body, to 3~12. When there are more than 12 bent parts 30 provided at each end of the stent body, the size of the diamond-shaped meshes 20 is greatly reduced regardless of the diameter of the wires 10 and 11, so that it is almost impossible to reduce the volume of the stent body to a desired level when inserting the stent into a desired part of a contracted muscular passage or a dilated artery. When the number of the bent parts 30 provided at each end of the stent body is less than three, it is possible to reduce the volume of the stent body to a desired level when inserting the stent into the desired part of the contracted muscular passage or the dilated artery. However, in such a case, the stent has insufficient elasticity, so that the stent may fail to restore its original shape after the stent is inserted into the desired part of the contracted muscular passage or the dilated artery. Therefore, it is preferred to have between 3 and 12 bent parts 30.

The flexible self-expandable stent is placed in a desired part of a contracted muscular passage or a dilated artery in a manner similar to that described for the conventional stents. In addition, when the flexible self-expandable stent is placed in the contracted or dilated part of the muscular passage or the artery, the stent maintains its shape corresponding to the shape of the contracted or dilated part, regardless of a horizontal straight shape, a vertical straight shape or a bent shape of the contracted or dilated part, as shown in FIG. 4. The stent is thus effectively used for opening the contracted part or repairing the arterial dilatation, without deforming the shape of the contracted muscular passage, the contracted blood vessel, or the dilated artery.

In the flexible self-expandable stent, the net-like structure 50 of the cylindrical stent body has high flexibility which allows the stent body to be easily shaped as desired in response to an external force and maintain the shape in the contracted or dilated part of the body, since the net-like structure 50 is produced by knitting the wires 10 and 11 with each other to form the interlocked points 60, and the diameter φ of the stent body is set to a range which gives the desired elasticity to the stent body.

However, the flexible self-expandable stent is problematic in that the stent may not prevent an infiltration of tumor cells into the interior of the stent, or prevent undesired contact of a material, such as food, with the lesion, or repair the arterial dilatation. Therefore, it is necessary to form a coat layer on the external surface of the stent body to externally cover the sidewall of the stent body.

When the coat layer is formed on the external surface of the stent body to externally cover the sidewall of the stent body, the coat layer is integrated with the stent body into a single structure. In such a case, the flexible self-expandable stent may not take the desired shape in response to an external force or maintain the shape in the contracted or dilated part of the body.

SUMMARY OF THE INVENTION

Accordingly, the present invention has been made keeping in mind the above problems occurring in the prior art, and an object of the present invention is to provide a flexible self-expandable stent, which is set within the desired part of a contracted muscular passage, a contracted blood vessel having a lesion, or an artery having an aneurysm to open the contracted part or repair the arterial dilatation, without deforming the shape of the desired part of the contracted muscular passage, the contracted blood vessel, or the dilated artery, and which prevents an infiltration of tumor cells into the interior of the stent and prevents an undesired contact of a material, such as food, with the lesion, and which reliably repairs the arterial dilatation.

In order to accomplish the above object, the present invention provides a flexible self-expandable stent, comprising: hollow cylindrical inside and outside stent bodies fabricated by knitting first and second super-elastic shape memory alloy wires to make a net-like structure of each of the inside and outside stent bodies in that the first wire, which is zigzagged with a diagonal length P in a longitudinal direction of each of the inside and outside stent bodies, is interlocked with the second wire, which is zigzagged with a diagonal length 2P in the longitudinal direction, at different positions to form a plurality of interlocked points capable of allowing each of the inside and outside stent bodies to contract and expand in the longitudinal direction, with a plurality of intersecting points being formed by a repeated intersection of the first and second wires at a plurality of positions between the interlocked points to allow each of the inside and outside stent bodies to apply a force against the longitudinal contraction thereof, and a plurality of diamond-shaped meshes being defined by the interlocked points and the intersecting points, the first and second wires being thus interlocked with each other to be prevented from being separated from each other while allowing each of the inside and outside stent bodies to contract and expand; and a hollow rubber tube closely fitted between the inside and outside stent bodies, the hollow rubber tube having a length similar to a length of each of the inside and outside stent bodies, with each of overlapped ends of the rubber tube and the inside and outside stent bodies being integrating into a single structure.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
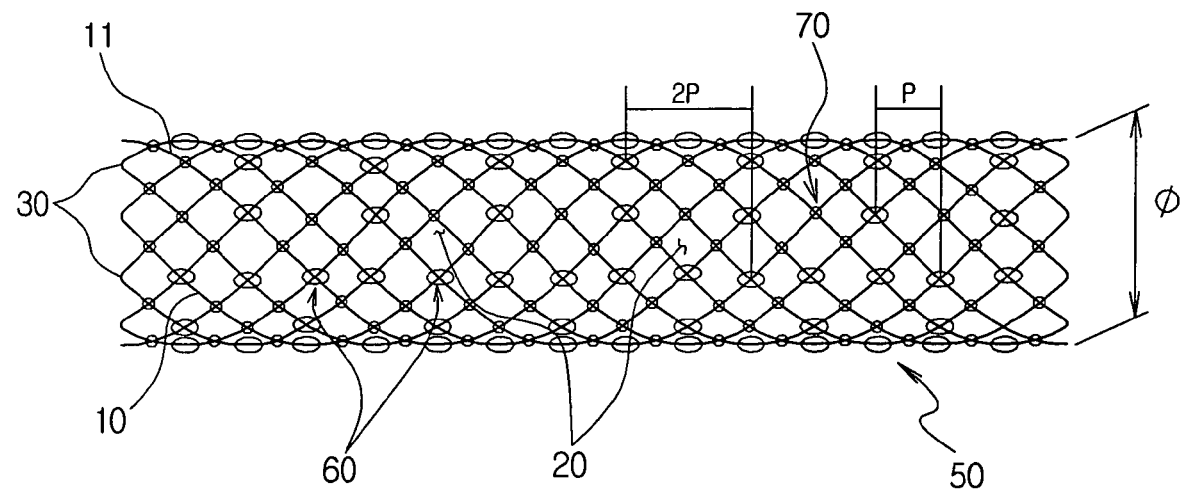
FIG. 1 is a front view of a conventional flexible self-expandable stent proposed by the inventor of this invention.

Reference now should be made to the drawings, in which the same reference numerals are used throughout the different drawings to designate the same or similar components.

Figure 2:
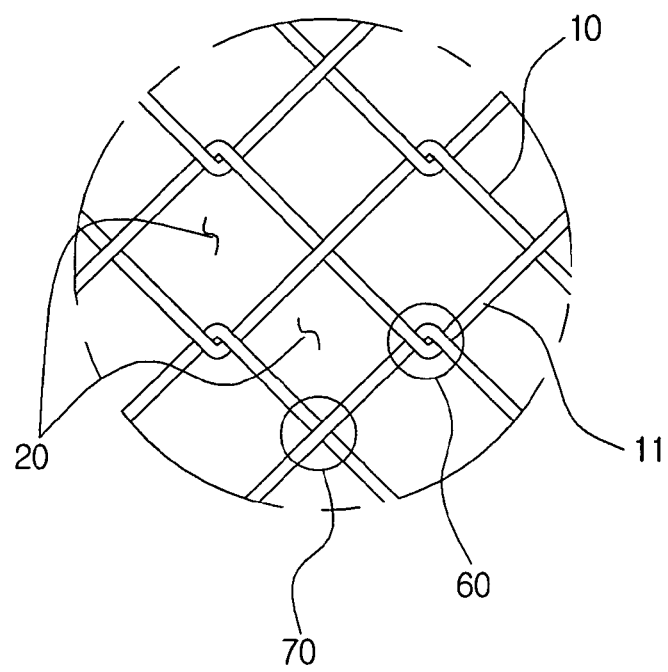
FIG. 2 is an enlarged view of a part of the stent of FIG. 1 to show a net-like structure with a plurality of diamond-shaped meshes of the stent.
Figure 3:
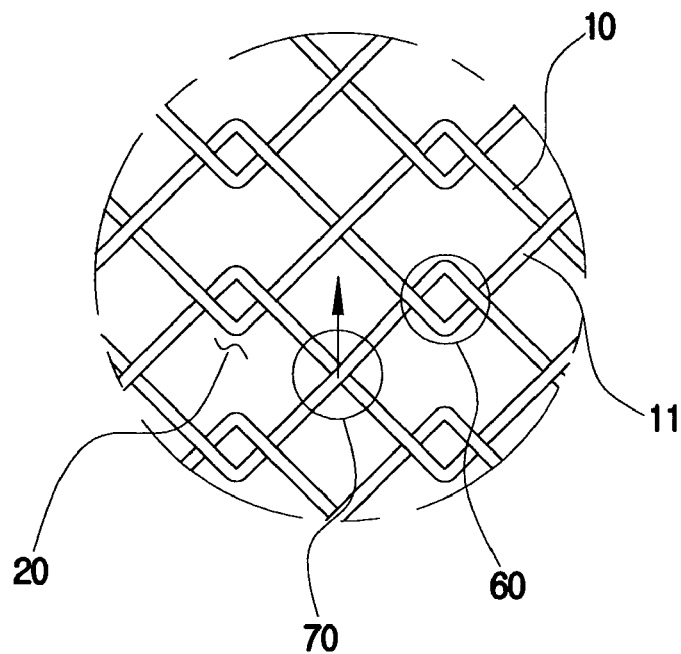
FIG. 3 is a view corresponding to FIG. 2, but showing an operation of the net-like structure with the diamond-shaped meshes of the stent.
Figure 4:
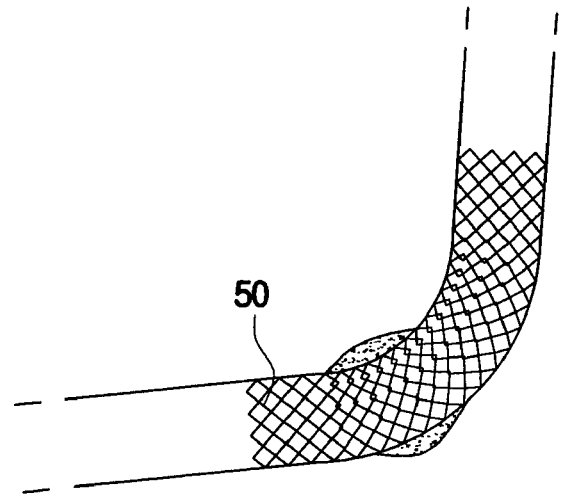
FIG. 4 is a view, showing the stent of FIG. 1 set within a contracted passage of the body.
Figure 5:
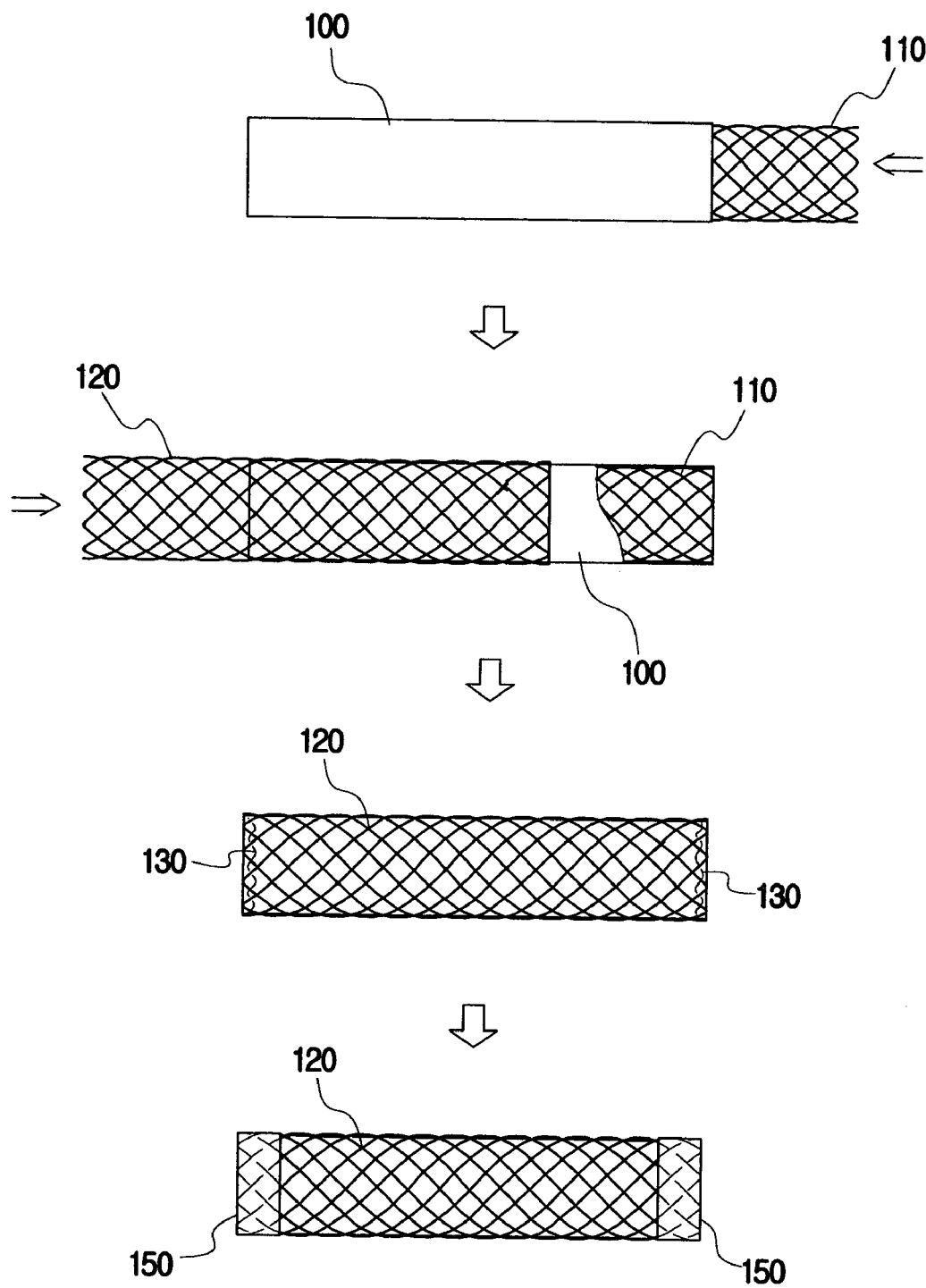
FIGS. 5A to 5D are views showing a process of fabricating a flexible self-expandable stent, according to an embodiment of the present invention.
Figure 5A:
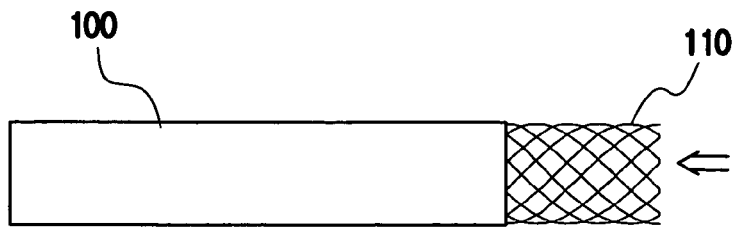
Figure 5B:
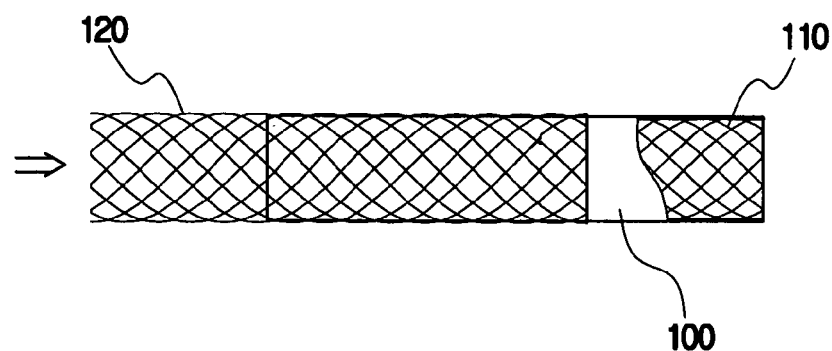
Figure 5C:
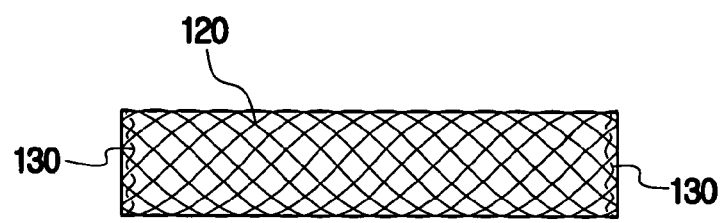
Figure 5D:
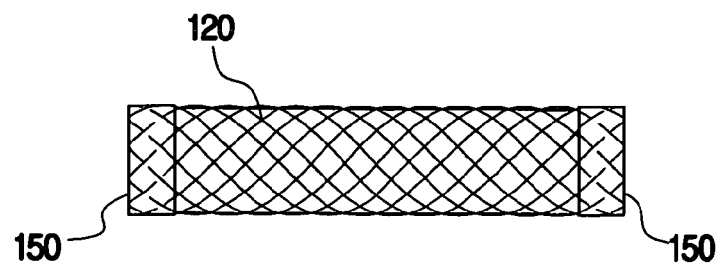

A flexible self-expandable stent according to the present invention comprises hollow cylindrical inside and outside stent bodies 110 and 120, with a hollow rubber tube 100 closely fitted between the inside and outside stent bodies 110 and 120. The hollow cylindrical inside and outside stent bodies 110 and 120 each have the same net-like structure as that of the conventional flexible self-expandable stent of FIGS. 1 to 3. That is, as shown in FIGS. 1 to 3, each of the inside and outside stent bodies 110 and 120 is fabricated by knitting first and second super-elastic shape memory alloy wires 10 and 11 to make a net-like structure 50 in that the first wire 10, which is zigzagged with a diagonal length P in a longitudinal direction of each of the inside and outside stent bodies 110 and 120, is interlocked with the second wire 11, which is zigzagged with a diagonal length 2P in the longitudinal direction, at different positions to form a plurality of interlocked points 60 capable of allowing each of the inside and outside stent bodies 110 and 120 to contract and expand in the longitudinal direction. In the net-like structure 50, a plurality of intersecting points 70 are formed by a repeated intersection of the first and second wires 10 and 11 at a plurality of positions between the interlocked points 60 to allow each of the inside and outside stent bodies 110 and 120 to apply a force against the longitudinal contraction thereof. In the net-like structure 50, the interlocked points 60 and the intersecting points 70 define a plurality of diamond-shaped meshes 20. The first and second wires 10 and 11 are thus interlocked with each other to be prevented from being separated from each other while allowing each of the inside and outside stent bodies 110 and 120 to contract and expand.

After fabricating the inside and outside stent bodies 110 and 120 through the above-described manner, the hollow rubber tube 100 having a length roughly equal to that of each of the inside and outside stent bodies 110 and 120 and made of a resin material, such as polytetrafluoroethylene (PTFE), is prepared.

After preparing the inside and outside stent bodies 110 and 120, and the hollow rubber tube 100, the desired flexible self-expandable stent is produced by integrating the stent bodies 110 and 120, and the rubber tube 100 into a single body. The process of producing the flexible self-expandable stent by integrating the stent bodies 110 and 120, and the rubber tube 100 will be described herein below, with reference to FIGS. 5A to 5D.

First, the hollow rubber tube 100 is closely fitted over the inside stent body 110, prior to placing the outside stent body 120 closely over the rubber tube 100.

Second, each of the overlapped ends of the rubber tube 100 and the inside and outside stent bodies 110 and 120 are integrated into a single structure, after the rubber tube 100 is closely disposed between the inside and outside stent bodies 110 and 120.

In order to integrate each of the overlapped ends of the rubber tube 100 and the inside and outside stent bodies 110 and 120 into the single structure, each of the overlapped ends of the rubber tube 100 and the inside and outside stent bodies 110 and 120 is sewn with a thread 130 by stitching each of the overlapped ends, thus forming a sewn end. After the sewing step, each of the sewn ends is immersed in a synthetic resin solution, such as a polyurethane solution, to form a resin-impregnated part 150 at each sewn end. Therefore, each of the overlapped ends of the rubber tube 100 and the inside and outside stent bodies 110 and 120 is integrated into the single structure, and the flexible self-expandable stent of the present invention is produced.

Figure 6:
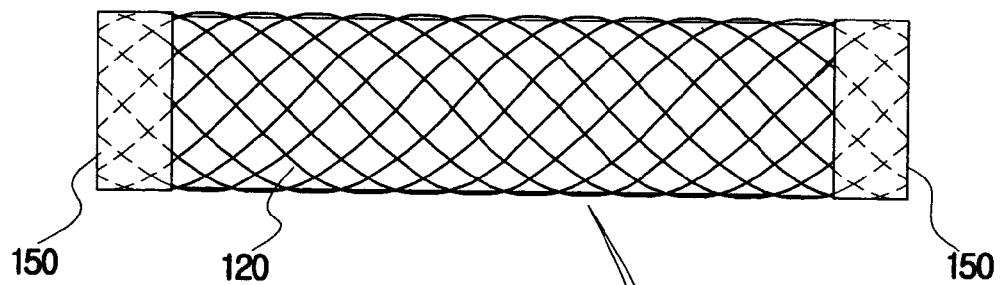
FIG. 6 is a front view of the flexible self-expandable stent which is produced through the process of the present invention.
Figure 6:
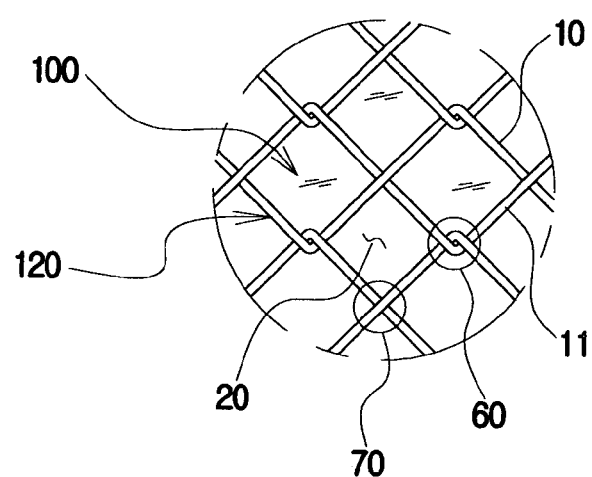
Figure 7:
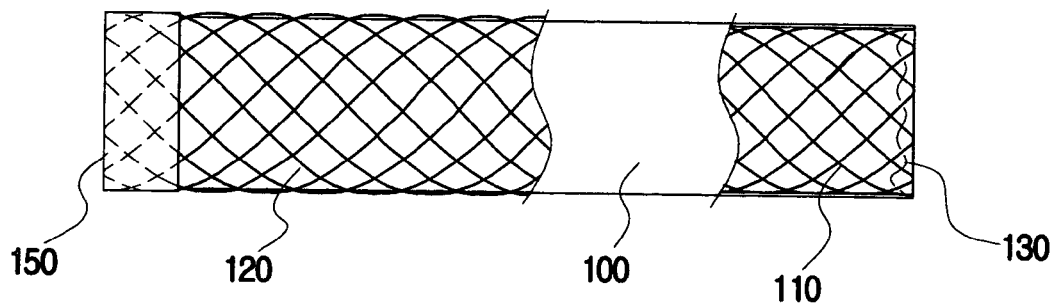
FIG. 7 is a partially broken front view of the stent of FIG. 6.
Figure 8:
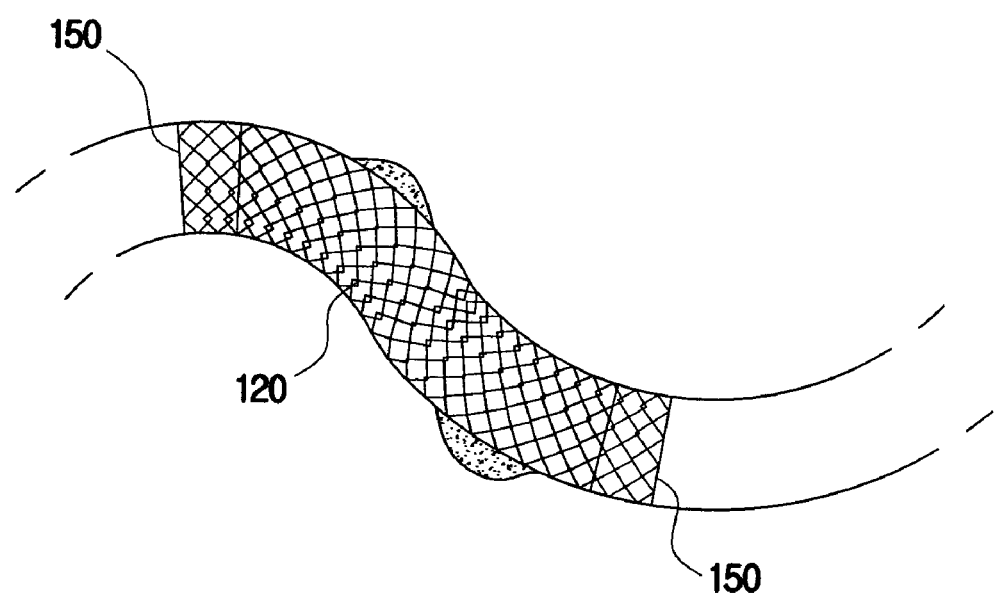
FIG. 8 is a view, showing the stent of FIG. 6 set within a contracted passage of the body.

The construction of the flexible self-expandable stent is shown in FIG. 6 which is a front view of the flexible self-expandable stent, and in FIG. 7 which is a partially broken front view of the stent of FIG. 6.

As shown in FIGS. 6 and 7, the flexible self-expandable stent of the present invention includes the hollow cylindrical inside and outside stent bodies 110 and 120. Each of the hollow cylindrical inside and outside stent bodies 110 and 120 is fabricated by knitting the first and second super-elastic shape memory alloy wires 10 and 11 to make the net-like structure 50 in that the first wire 10, zigzagged with the diagonal length P in the longitudinal direction of each of the inside and outside stent bodies 110 and 120, is interlocked with the second wire 11 which is zigzagged with the diagonal length 2P in the longitudinal direction, at different positions to form the interlocked points 60 capable of allowing each of the inside and outside stent bodies 110 and 120 to contract and expand in the longitudinal direction. In the net-like structure 50, the first and second wires 10 and 11 repeatedly intersect each other at a plurality of positions between the interlocked points 60, thus forming the intersecting points 70 which allow each of the inside and outside stent bodies 110 and 120 to apply a force against the longitudinal contraction of each stent body 110, 120. The net-like structure 50 is thus provided with the diamond-shaped meshes 20 which are defined by the interlocked points 60 and the intersecting points 70. In the net-like structure 50, the first and second wires 10 and 11 are thus interlocked with each other to be prevented from being separated from each other while allowing each of the inside and outside stent bodies 110 and 120 to contract and expand.

The hollow rubber tube 100 is closely fitted between the inside and outside stent bodies 110 and 120. In such a case, the length of the hollow rubber tube 100 is similar to that of each of the inside and outside stent bodies 110 and 120. Each of the overlapped ends of the rubber tube 100 and the inside and outside stent bodies 110 and 120 is integrating into a single structure.

In such a case, each of the overlapped ends of the rubber tube 100 and the inside and outside stent bodies 110 and 120 is sewn with the thread 130 by stitching to form the sewn end. The sewn end is immersed in the polyurethane solution to form the resin-impregnated part 150, so that each of the overlapped ends is integrated into the single structure.

The flexible self-expandable stent of the present invention is used for insertion in the desired parts of contracted muscular passages, contracted blood vessels, or arteries having an aneurysm so as to open the contracted parts or repair the arterial dilatation, in the same manner as the conventional flexible self-expandable stents.

Since the flexible self-expandable stent of the present invention has a triple-layered structure which comprises the rubber tube 100 and the inside and outside stent bodies 110 and 120, the stent is effectively bent to a shape corresponding to the desired bent part of a contracted muscular passage, a contracted blood vessel, or an artery having an aneurysm. In addition, each of the overlapped ends of the rubber tube 100 and the inside and outside stent bodies 110 and 120 is integrated into a single structure by sewing the overlapped ends with the threads 130, and by immersing the sewn ends in the synthetic resin solution to form the resin-impregnated part 150 at each of the sewn ends. Therefore, the flexible self-expandable stent of the present invention is used for the insertion in the desired part of the contracted muscular passage, the contracted blood vessel, or the artery having an aneurysm so as to open the contracted part or repair the arterial dilatation, in the same manner as the conventional flexible self-expandable stents.

In each of the inside and outside stent bodies 110 and 120, the first and second zigzagged wires 10 and 11 are knitted with each other to produce the net-like structure 50 having the interlocked points 60 at which the wires 10 and 11 are movable relative to each other in response to an external force imposed on the net-like structure 50. Therefore, the stent of the present invention maintains a bent shape thereof within a bent part of a contracted muscular passage, a contracted blood vessel, or an artery with an aneurysm, thus being effectively used for opening the contracted bent part or repair the arterial dilatation, without deforming the shape of the bent part of the muscular passage, the blood vessel, or the dilated artery.

The rubber tube 100, which is fitted between the inside and outside stent bodies 110 and 120, reliably prevents tumor cells from infiltrating into the interior of the stent through the meshes 20 of the stent bodies 110 and 120. The rubber tube 100 also prevents a material, such as food, from coming into contact with the lesion of a contracted muscular passage of the body when the material passes through the contracted passage, and repairs an arterial dilatation.

In the present invention, it is possible to produce a flexible self-expandable stent by placing only one stent body 110 or 120 having the net-like structure, inside or outside the rubber tube 100. However, in the stent having one stent body, a return force applied in the rubber tube 100 elastically restores an original shape of the rubber tube 100 after the stent is installed in a desired bent part of the contracted muscular passage, the contracted blood vessel, or the artery with the aneurysm while being bent to correspond to the bent shape of the lesion. The stent having only one stent body 110 or 120 may fail to maintain its bent shape, so that the inside and outside stent bodies 110 and 120 are preferably placed around the rubber tube 100 to form the triple-layered structure of the stent. The stent of the present invention thus maintains its bent shape regardless of the bent shape of the rubber tube 100.

As described above, the present invention provides a flexible self-expandable stent which comprises inside and outside stent bodies, and a rubber tube fitted between the inside and outside stent bodies, with each of the overlapped ends of the rubber tube and the inside and outside stent bodies being integrated into a single structure. The stent is used for the insertion in a desired part of a contracted muscular passage, a contracted blood vessel, or an artery with an aneurysm so as to open the contracted part or repair the arterial dilatation. The stent maintains its shape within the desired part of the contracted muscular passage, the contracted blood vessel, or the artery having the aneurysm, regardless of the shape of the desired part, which is a vertical linear shape, a horizontal linear shape, or a bent shape, thus being effectively used for opening the contracted part or repair the arterial dilatation, without deforming the shape of the contracted part or the dilated artery. The stent also reliably prevents tumor cells from infiltrating into the interior of the stent through the meshes of the stent bodies, and prevents a material, such as food, from coming into contact with the lesion of the contracted part when the material passes through the contracted part, and repairs the arterial dilatation.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A flexible self-expandable stent, comprising:

hollow cylindrical inside and outside stent bodies fabricated by knitting first and second super-elastic shape memory alloy wires to make a net-like structure of each of the inside and outside stent bodies in that the first wire, which is zigzagged with a diagonal length P in a longitudinal direction of each of the inside and outside stent bodies, is interlocked with the second wire, which is zigzagged with a diagonal length 2P in the longitudinal direction, at different positions to form a plurality of interlocked points capable of allowing each of the inside and outside stent bodies to contract and expand in the longitudinal direction, with a plurality of intersecting points being formed by repeated intersection of the first and second wires at a plurality of positions between the interlocked points to allow each of the inside and outside stent bodies to apply a force against the longitudinal contraction thereof, and plurality of diamond-shaped meshes being defined by the interlocked points and the intersecting points, the first and second wires being thus interlocked with each other to be prevented form being separated from each other while allowing each of the inside and outside stent bodies to contract and expand; and a hollow rubber tube closely fitted between the inside and outside stent bodies, the hollow rubber tube having a length substantially equal to a length of each of the inside and outside stent bodies, wherein both distal and proximal ends of the rubber tube and the inside and outside stent bodies are intergrated into a single structure, wherein each the distal and proximal ends of the rubber tube and the inside and outside stent bodies is sewn with a thread by stitching to form a sewn end, and the sewn end is immersed in a polyurethane solution to form a resin-impregnated part, thus being integrated into the single structure.

2. A flexible self-expandable stent, comprising:

a hollow cylindrical inside and outside stent bodies each comprising first and second super-elastic shape memory alloy wires knitted into a net-like structure with the first wire zigzagged with a diagonal length P in a longitudinal direction and the second wire zigzagged with a diagonal length 2P in the longitudinal direction at a plurality of interlocked points in the longitudinal direction with intersecting points between the interlocked points; and a hollow rubber tube closely fitted between the inside and outside stent bodies, wherein distal and proximal ends of the rubber tube and the inside and outside stent bodies are held together with thread stitching and an impregnated polyurethane.

* * * * *